US008562571B2

(12) United States Patent  
Mudd

(10) Patent No.: US 8,562,571 B2  
(45) Date of Patent: Oct. 22, 2013

(54) SLOTTED SYRINGE

(75) Inventor: Christopher S. Mudd, Ventura, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/604,896

(22) Filed: Sep. 6, 2012

(65) Prior Publication Data

US 2012/0330245 A1    Dec. 27, 2012

Related U.S. Application Data

(62) Division of application No. 12/942,373, filed on Nov. 9, 2010.

(60) Provisional application No. 61/267,271, filed on Dec. 7, 2009.

(51) Int. Cl.  
*A61M 5/315* (2006.01)

(52) U.S. Cl.  
USPC ......................................................... 604/218

(58) Field of Classification Search  
USPC ............ 604/110, 111, 164.05, 187, 218, 220, 604/227  
See application file for complete search history.

(56) References Cited

U.S. PATENT DOCUMENTS

| 1,331,805 | A  | * | 2/1920  | Chance ......................... 604/227 |
| 6,368,308 | B1 | * | 4/2002  | Nerney ......................... 604/227 |
| 6,972,004 | B2 | * | 12/2005 | La ................................. 604/187 |
| 2006/0122561 | A1 | * | 6/2006 | Ray ............................... 604/110 |

* cited by examiner

*Primary Examiner* — Kami A Bosworth  
(74) *Attorney, Agent, or Firm* — Linda Fox; Stephen Donovan; Debra Condino

(57) ABSTRACT

A syringe is disclosed. The syringe may include a syringe body, a first slot formed in the syringe body, a first sleeve covering the first slot, a thumb grip including a first slot guide disposed in the first slot, the thumb grip shaped to slide from a first position near the distal end of the syringe body toward a second position near the proximal end of the syringe body, and a plunger disposed in the fluid chamber of the syringe body. The plunger is configured to move towards the proximal end of the syringe body in response to pressure applied by a user to the thumb grip and includes a first plunger slot guide.

2 Claims, 14 Drawing Sheets

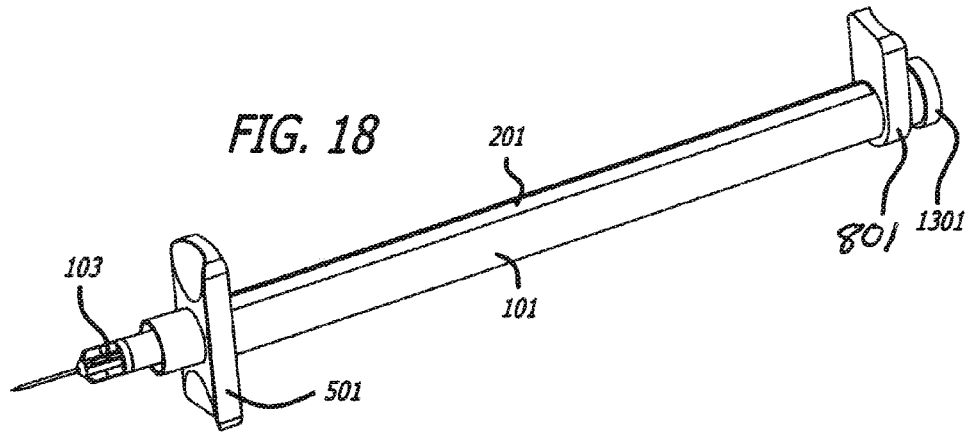
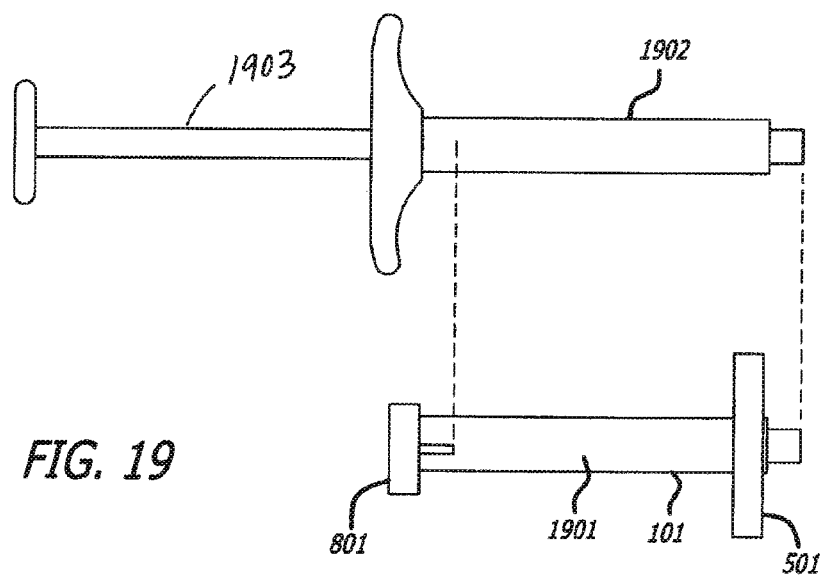

SLOTTED SYRINGE

RELATED APPLICATION

This application is a divisional of U.S. patent application Ser. No. 12/942,373, filed Nov. 9, 2010, which claims priority to U.S. Provisional Patent Application No. 61/267,271, filed on Dec. 7, 2009, the entire disclosure of which is incorporated herein by this reference.

BACKGROUND

A number of medical applications require the injection of significant amounts of material. For example, one such application is the injection of dermal fillers to correct facial wrinkles or folds. In such a procedure, a possibly significant quantity of dermal filler material is injected under the skin using a syringe. In addition, the material injected may have a higher viscosity than the substances typically injected by syringe. For example, some dermal fillers may include gels, such as a gel made of hyaluronic acid. Traditional syringes and the plunger rods used with such syringes present a number of problems when used for such applications. For instance, in order to accommodate significant volumes of material, such syringes must typically have either a large length or cross-sectional area. Syringes with larger cross-sectional areas are often not practical, however, because the extrusion force required in operating a syringe increases with the cross-sectional area, this may be particularly problematic when injecting viscous fluids. Increasing the length of a traditional syringe, however, may significantly increase the overall length of the device, as a longer plunger may also need to be used, which may reduce the user's comfort and control during use. Accordingly, example embodiments described herein provide improved syringe devices which may address a number of the shortcomings of traditional devices.

SUMMARY

Some example embodiments described herein provide a syringe, which may include a syringe body with a fluid chamber, the syringe body having a distal end and a proximal end, sometimes hereinafter referred to as the luer end. The proximal end includes an extrusion opening. The syringe further comprises a first slot formed in the syringe body, starting near the proximal end of the syringe body and ending near the distal end of the syringe body; a first sleeve covering the first slot; a thumb grip, the thumb grip including a first slot guide disposed in the first slot, the thumb grip shaped to slide from a first position near the distal end of the syringe body toward a second position near the proximal end of the syringe body; and a plunger disposed in the fluid chamber of the syringe body, the plunger configured to move towards the proximal end of the syringe body in response to pressure applied by a user to the thumb grip, the plunger including a first plunger slot guide disposed in the first slot.

Some example embodiments may also include a second slot formed in the syringe body, beginning near the proximal end of the syringe body and ending near the distal end of the syringe body; and a second sleeve covering the second slot; where the thumb grip may further include a second slot guide disposed in the second slot.

In some example embodiments, the first sleeve and the second sleeve may be parts of a single unitary sleeve covering the syringe body. In other example embodiments, the first slot may pass through the syringe body, from an outer surface forming an outer circumference of the syringe body through an inner surface forming the fluid chamber.

In some example embodiments, the first sleeve may be an integral part of the syringe body. In other example embodiments, the first sleeve may be affixed to the syringe body.

In some example embodiments, the first sleeve may be attached to the syringe body by one of co-molding, overmolding, press-fitting, laminating, adhering, welding, and shrink wrapping.

In some example embodiments, the plunger is attached to the thumb grip. Other example embodiments may also include an end cap disposed at the distal end of the syringe body. Further, some example embodiments may also include a cutting edge attached to a proximal end of the thumb grip and positioned to cut the first sleeve as the thumb grip moves towards the proximal end of the syringe body.

Some example embodiments may also include a finger grip disposed on the syringe body near the proximal end of the syringe body. Other example embodiments may also include an intermediate finger grip disposed on the syringe body between the thumb grip and the finger grip.

In some example embodiments, the intermediate finger grip may be configured to slide towards the proximal end of the syringe body when pushed by the thumb grip.

In some example embodiments, the intermediate finger grip may include an intermediate finger grip body shaped to support a user's finger; and an aperture passing from a proximal side of the intermediate finger grip body to a distal side of the intermediate finger grip body, in which the syringe body is disposed.

In some example embodiments, the intermediate finger grip may be configured to be removed from the syringe body during operation.

In some example embodiments, the intermediate finger grip may include a finger grip body shaped to support a user's finger; and a clip formed on an end of the finger grip in which the syringe body is disposed.

In some example embodiments, the first sleeve may be made from the same material as the syringe body. In other example embodiments, the first sleeve may be made from different material than the syringe body. In still other example embodiments, the first slot may extend to the distal end of the syringe body.

In addition, some example embodiments may provide a syringe, which may include a syringe body with a fluid chamber, the syringe body having a proximal end and a distal end, with an extrusion opening at the proximal end; a first slot formed in the syringe body, beginning near the proximal end of the syringe body and ending near the distal end of the syringe body; a second slot formed in the syringe body, beginning near the proximal end of the syringe body and ending near the distal end of the syringe body; a first sleeve covering the first slot; a second sleeve covering the second slot; a thumb grip including a first slot guide and a second slot guide, the slot guides disposed in the slots, the thumb grip shaped to slide from a first position near the distal end of the syringe body toward a second position near the proximal end of the syringe body; a first and second cutting edge disposed on a proximal side of the thumb grip and positioned to cut the first and second sleeve as the thumb grip moves towards the proximal end of the syringe body; a finger grip disposed on the syringe body, near the proximal end of the syringe body; and a plunger disposed within the fluid chamber of the syringe body, the plunger configured to move towards the proximal end of the syringe body in response to pressure applied by a user to the thumb grip, the plunger including a first and second plunger slot guide disposed in the first and second slots. Example embodiments may also include an intermediate finger grip, disposed on the syringe body, between the finger grip and the thumb grip.

BRIEF DESCRIPTION OF THE DRAWINGS

The present invention will be more readily understood from a detailed description of example embodiments taken in conjunction with the following figures:

FIG. 18 illustrates an example syringe in accordance with an example embodiment.

FIG. 19 illustrates an example syringe in accordance with an example embodiment, with a traditional syringe.

DETAILED DESCRIPTION

As explained above, a number of medical and cosmetic procedures involve the injection of significant volumes of liquids, gels, and other fluids, e.g. dermal fillers. In order to accommodate such volumes, it is typically necessary to use a syringe with a large diameter, a large length, or both. Syringes with larger diameters are, however, often impractical, especially when used with higher viscosity fluids, as the extrusion force required to operated the syringe increases as the diameter of the syringe increases. Increasing the length of the syringe, however, can also result in practical issues, e.g. reduced functionality, ergonomics considerations, and less control over the needle that can not only cause physician discomfort, but ultimately affect the patient's safety. For example, as the length of a syringe increases, the finger span required to operate the syringe also typically increases, which may result in reduced user comfort and control. In addition, the distance at which the user is required to hold the syringe from the injection site is also increased, which again can lead to loss of control, and possibly patient injury. Example embodiments may address such problems by providing syringes designed to reduce the overall length of the syringe without reducing the volume of fluid which may be injected using the syringe.

For example, some embodiments may provide for a single-use, slotted syringe that will allow the operator to easily inject low to high viscosity gels or fluids, without the use of plunger rod. Such example embodiments may provide a number of advantages over traditional syringe and plunger rod systems. For example, users may be provided with greater control compared to a standard medical syringe, as the plunger rod, and its corresponding length are eliminated. Example embodiments may also allow users to more easily hold, manipulate, and operate the device with two or three fingers. Further, some example embodiments may result in a shorter syringe, as compared to an equivalent volume standard medical syringe, which may allow the operator to get closer to the area of injection for more control during injection. The example embodiments may also allow the syringe to accommodate a larger injection volume without increasing the inner diameter of the syringe, thus keeping the injection force low.

Figure 1:
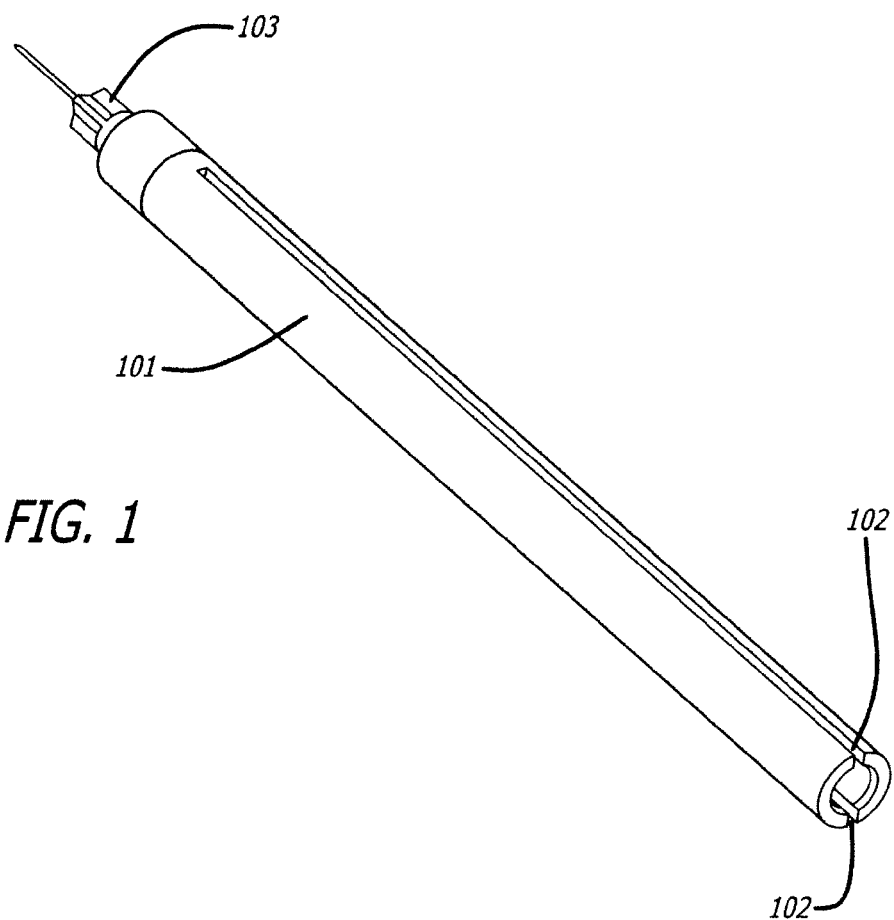
FIG. 1 illustrates an example syringe body in accordance with an example embodiment.

Such example embodiments may include a syringe body, as illustrated in FIG. 1. The syringe body 101 can be generally of standard design, and may be made of materials used in common sterile, single-use syringes. The syringe body 101 can be any size (i.e. length, inner diameter, outer diameter, wall thickness volume, etc.), and may have any suitable shape, e.g., may be generally cylindrical, may have an oval cross-section, or may have the cross-section of a rectangle or other polygon. In addition, the syringe body 101 may have a needle 103 attached to it, or may provide a standard mounting for a needle 103. For instance, the syringe body 101 may provide a standard luer slip or luer lock attachment.

Unlike a standard syringe, however, example embodiments may include one or more slots 102 running along the axis of the syringe body 101. Such slots 102 may completely penetrate through the wall of the syringe body 101. In some embodiments, the slots 102 may extend from a region near a proximal end of the syringe body 101, to a distal end of the syringe body 101 (the terms proximal and distal, as used herein, are to be understood in relation to the point of injection during use).

A sleeve may also be provided, which may fit over the syringe body 101, covering the slots 102. The purpose of the sleeve may be to fill the voids left by the slots 102, in order to prevent fluids contained in the chamber of the syringe body 101, when in use, from escaping through the slots 102, and to assist in providing a sterile barrier. The sleeve may be attached to the syringe body 101 using one or more methods, including, but not limited to co-molding, overmolding, press-fitting, laminating, adhering, welding, and/or shrink wrapping. The sleeve may be comprised of materials which are somewhat flexible and can be easily cut with a sharp edge or blade, yet are rigid enough to retain the round, or other, cross-section of the syringe body 101 and keep the injectable fluids inside the syringe body 101. For example, a suitable sleeve may be made of thermoplastic elastomer (TPE), silicone rubber, rubber, foil, or closed-cell foam, etc. It is noted that, in some example embodiments, the sleeve may be an integral part of the syringe body 101. In such examples, slots 102 may be formed in the syringe body 101 which pass only partially through the body 101.

Figure 2:
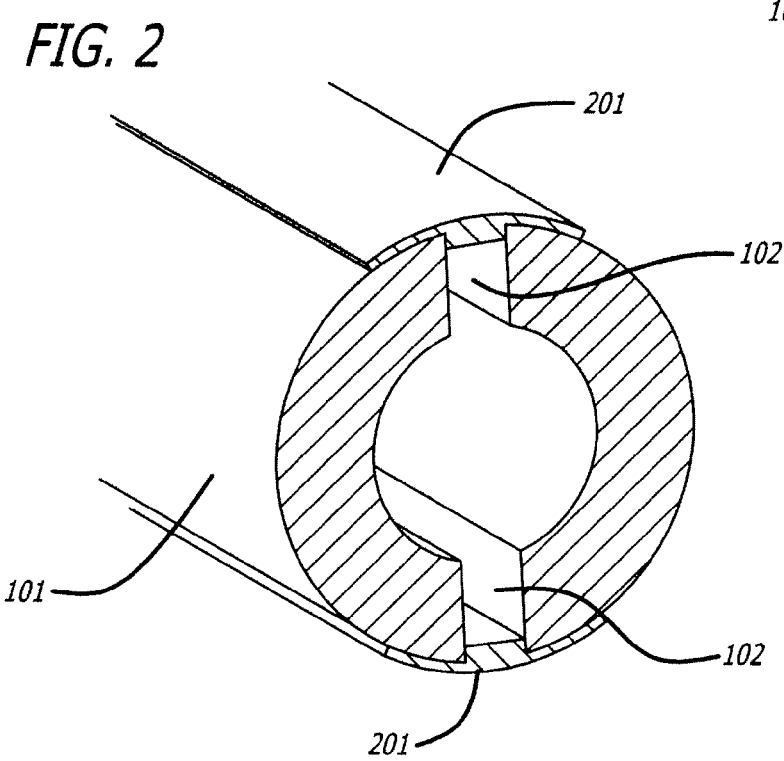
FIG. 2 illustrates a detailed view of an example syringe body in accordance with an example embodiment.
Figure 3:
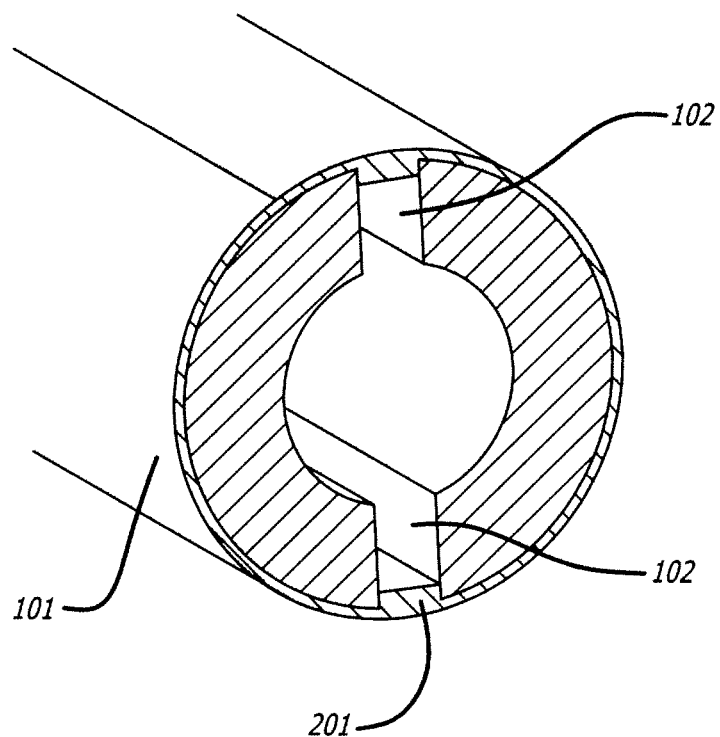
FIG. 3 illustrates a detailed view of an example syringe body in accordance with an example embodiment.
Figure 4:
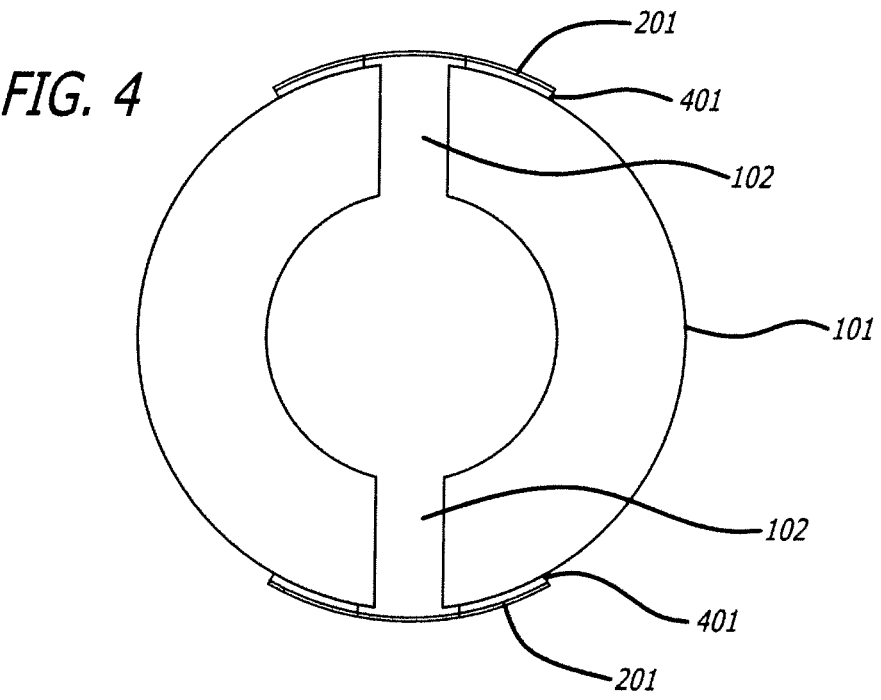
FIG. 4 illustrates a detailed view of an example syringe body in accordance with an example embodiment.

FIGS. 2-4 depict various syringe bodies 101 and sleeves in detail. For instance, FIG. 2 illustrates an example syringe body 101 with two slots 102. As shown, sleeve material 201 is attached over both of the slots 102. The illustrated material may have been attached by any of the mechanisms described above, or by other mechanisms. FIG. 3 similarly illustrates a syringe body 101 with two slots 102. Here, the slots 102 are covered by a sleeve 201 which is part of the syringe body 101. For example, such a sleeve 201 may be made of an over-molded layer. FIG. 4 shows another example syringe body 101 and sleeve 201. In the figure, the sleeve 201 is attached to the syringe body 101 by an adhesive layer 401.

Figure 5:
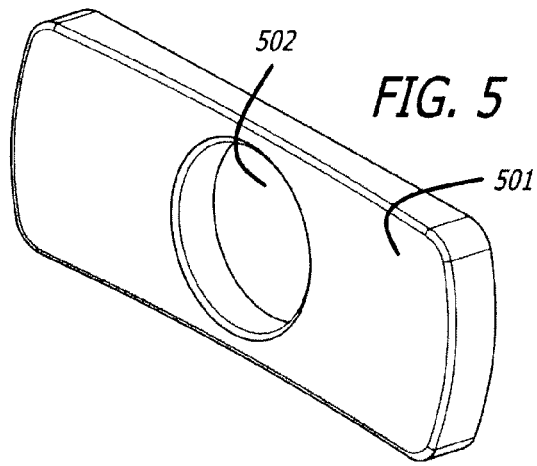
FIG. 5 illustrates a finger grip in accordance with an example embodiment.

Example embodiments may also include a finger grip, for example, as illustrated in FIG. 5. Again, the finger grip 501 can be of standard design, made of materials commonly used for traditional sterile, single-use syringe. The finger grip 501 can be molded or co-molded to the syringe body 101, or attached to the syringe body 101 using one or more methods, including, but not limited to, press-fitting, adhering and/or welding, etc. In example embodiments, such a finger grip 501 may be attached to the syringe body 101 near the proximal end or luer end of the syringe body 101. The finger grip 501 may provide a place for a user to place one or more fingers during use. For example, a finger grip may be provided which is generally rectangular in shape, possibly with rounded corners, and large enough to provide support for one or two fingers, although any other shape which can accommodate a user's fingers may also be used. In addition, the finger grip 501 may be designed to accommodate the syringe body 101, thus, for example, the finger grip of FIG. 5 includes an aperture 502 through which a syringe body 101 may pass.

Figure 6:
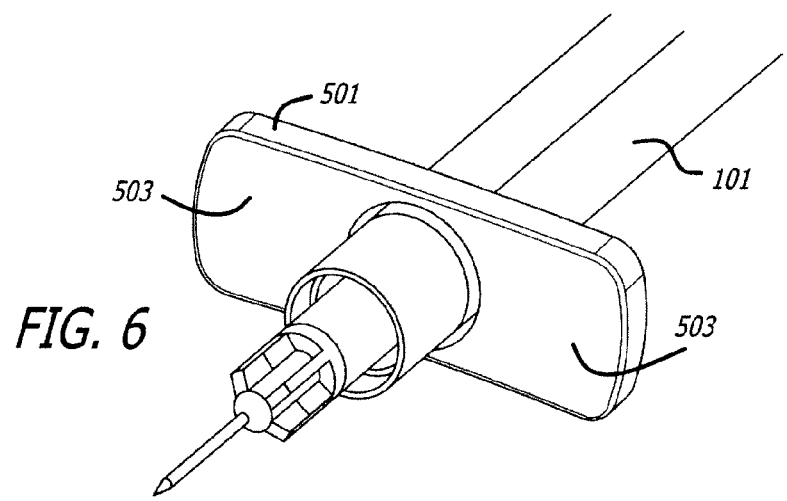
FIG. 6 illustrates an example finger grip and syringe body in accordance with an example embodiment.
Figure 7:
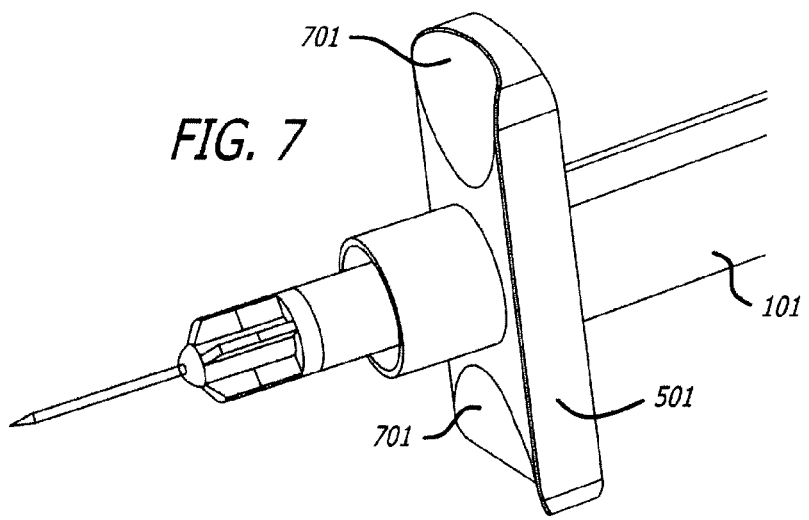
FIG. 7 illustrates an example finger grip and syringe body in accordance with an example embodiment.

An example finger grip 501 is shown attached to a syringe in FIG. 6. As illustrated, the finger grip 501 provides an aperture 502 in which the syringe body 101 is disposed. The finger grip 501 is attached to the syringe body 101 near the proximal end of the syringe body 101. In addition, the finger grip 501 provides positions 503 which may be used by one or more fingers, for example an index and middle finger. FIG. 7 illustrates another example finger grip 501. In the example, the finger grip 501 provides finger cups 701 shaped to comfortably accommodate a user's fingers, and to encourage the user to grip the syringe properly and securely.

Example embodiments may also include a thumb grip. Again, such thumb grips can be made of standard materials used for traditional sterile, single-use syringes. In example embodiments, the thumb grip may be designed to slide along the axis of the syringe body 101, from the distal end to the proximate end, when a user exerts forward pressure.

Example thumb grips may, in an initial state, be located on the syringe body 101, at or near the distal end of the syringe body 101. Such a thumb grip may allow a user to apply pressure to it, moving the thumb grip towards the proximal end of the syringe body 101. As the thumb grip slides forward, it may perform several functions. For example, the thumb grip may cut through the sleeve 201 in order to clear a path for its advance. Also, the thumb grip may advance a plunger, which, in turn, may apply pressure to the contents of the syringe causing the contents to be extruded through the needle 103.

Figure 8:
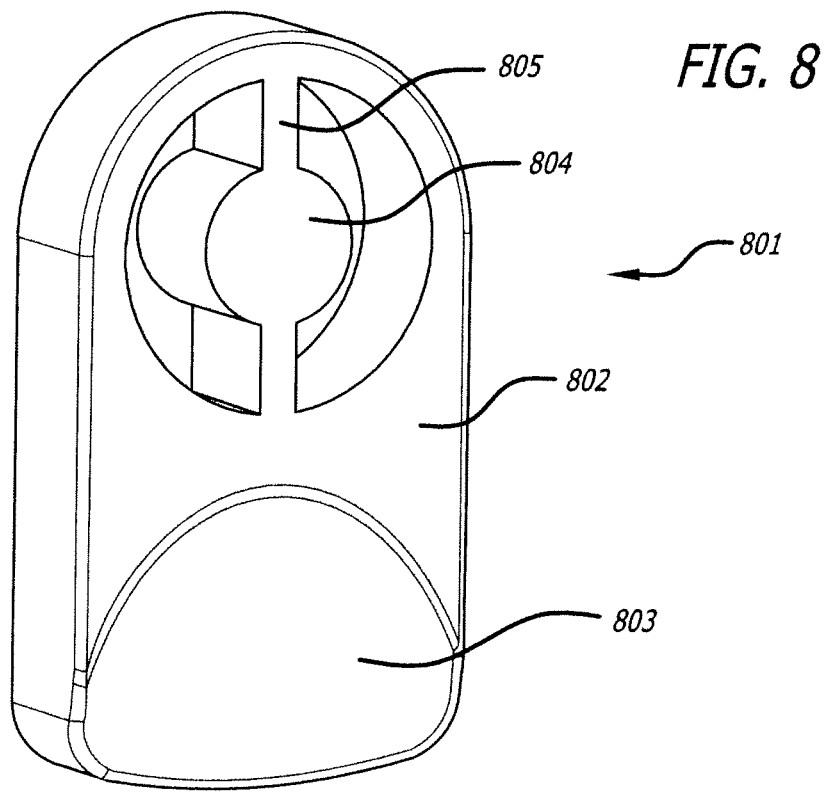
FIG. 8 illustrates an example thumb grip in accordance with an example embodiment.

FIG. 8 illustrates such a thumb grip 801. The example thumb grip 801 depicted includes a body 802, and a thumb grip cup formed or attached to the body 803. The body 802 of the thumb grip may again have any shape providing suitable support for a user's thumb. As illustrated, the thumb grip body 802 may have a generally rectangular shape, one end of which is rounded and semi-circular. A thumb grip cup 803 may provide a space for a user to apply pressure to the thumb grip 801. The thumb grip 801 may also have one or more apertures passing from a proximal side to a distal side of the thumb grip body 802, through which the syringe body 101 may pass. In addition, the example thumb grip 801 may include a plunger support 804, which may be used to push a plunger through the syringe, in operation. The plunger support 804 may be connected to the body 802 of the thumb grip 801 by one or more slot guides 805. For instance, as shown in the figure, the plunger support 804 may be suspended between two apertures by two slot guides 805. The slot guides 805 may fit within the slots 102 formed in the syringe body 101. Multiple slot guides 805 may be used, corresponding to the number, size, and position of the slots 102 in the syringe body 101. In addition, the features of the thumb grip 801 may be formed or molded as a single piece. Alternatively, the thumb grip 801 may be made from different pieces and possibly different materials. The thumb grip 801 is attached loosely to the syringe body 101 on the distal end thereof and is able to be slid distally by the user.

Figure 9:
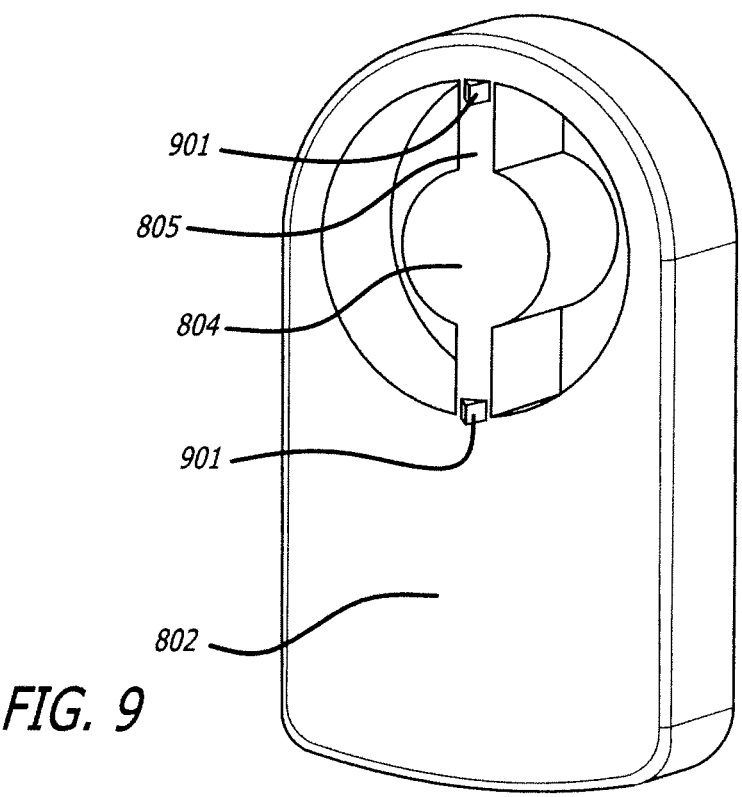
FIG. 9 illustrates an example thumb grip in accordance with an example embodiment.

The proximal side of an example thumb grip 801 is shown in FIG. 9. The example thumb grip 801 again includes the features described above. In addition, two cutting edges 901, or blades, are visible on the slot guides 805, though any number of cutting edges may be provided. These cutting edges 901 may be designed to cut through the sleeve 201, as the thumb grip 801 is pushed forward. Such blades 901 may be made of any material capable of cutting through the sleeve 201 and may be attached to the thumb grip 801 using any suitable method, or may be made together with the thumb grip 801 as a single piece. It is noted that, although not shown here, in example embodiments, a plunger may be fitted to this side of the thumb grip 801 in operation.

Figure 10:
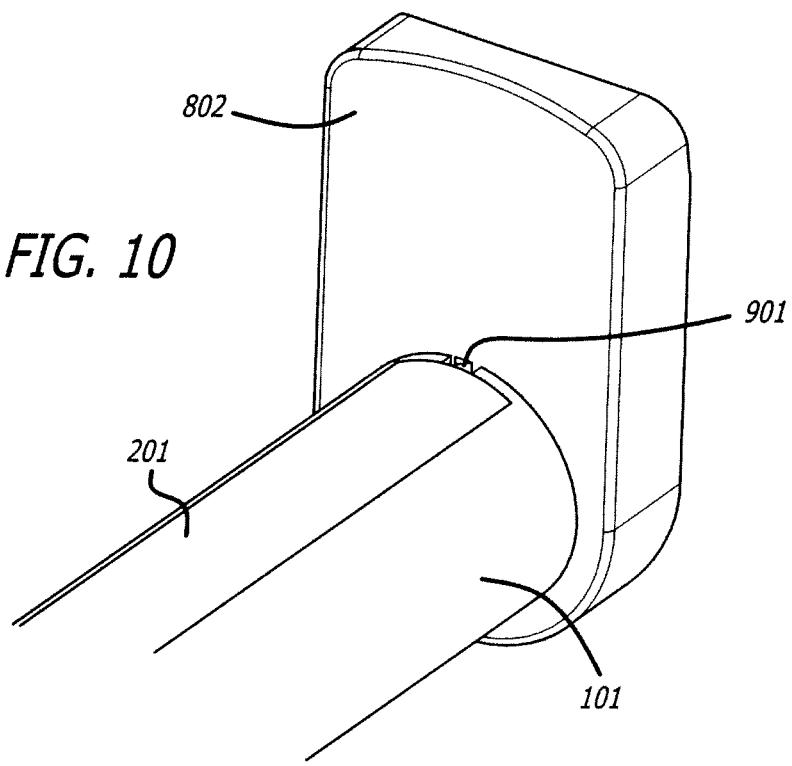
FIG. 10 illustrates an example thumb grip and syringe body in accordance with an example embodiment.

FIG. 10 shows an example thumb grip 801 placed on a syringe, in its initial position. Here, the thumb grip 801 is fit over the distal end of the syringe body 101, the slot guides 805 are aligned in or over the slots 102 in the syringe body 101, and the cutting edges 901 are aligned over the sleeve material 201. It is here noted, that the sleeve material 201 may or may not extend the complete length of the slots 102, on the distal end of the syringe body 101. When a user applies a force to the thumb grip 801, it may slide along the syringe body 101, extruding material from the syringe, and cutting the sleeve 201 as it moves. It is also noted that, in some embodiments, the sleeve 201 may not be cut. For instance, in alternative embodiments, the sleeve 201 may peel away from the syringe body 101 under suitable pressure.

Figure 11:
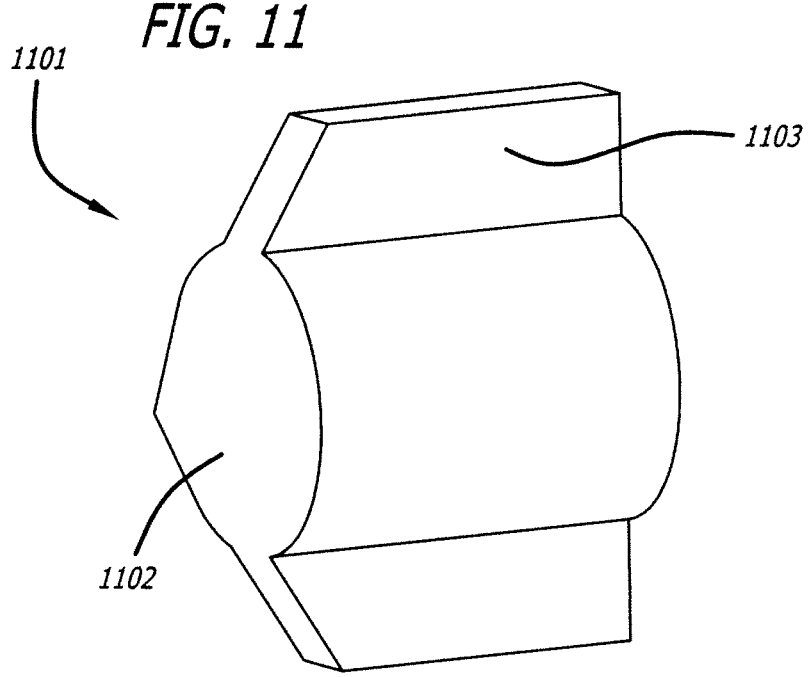
FIG. 11 illustrates an example plunger in accordance with an example embodiment.
Figure 12:
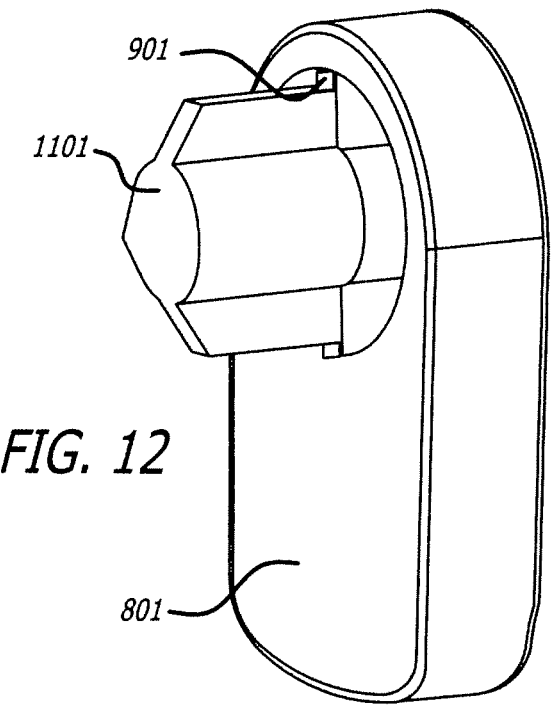
FIG. 12 illustrates an example plunger and thumb grip in accordance with an example embodiment.

As explained, a plunger may be attached to the thumb grip 801. The plunger may again be constructed of standard materials used for sterile, single-use syringes. FIG. 11 illustrates an example plunger 1101. The plunger 1101 may have a main body 1102, which may be shaped to fit within the chamber of the syringe body 101. In addition, the plunger 1101 may also have one or more slot guides 1103, matching the slots 102 in the syringe body 101. The slot guides 1103 may extend radially outward from the main body 1102 and may serve to push the injection material out of the slots 102 and into the main fluid chamber as it is being advanced towards the luer end. In example embodiments, the plunger 1101 may be attached to the thumb grip 801, or may be constructed together with the thumb grip 801 as a single piece, as shown in FIG. 12. In other embodiments, the plunger 1101 may not be attached to the thumb grip 801 at all, but may simply be pushed forward by the thumb grip 801 when in operation. The thumb grip 801 may be attached loosely to the syringe barrel on the distal end thereof.

Figure 13:
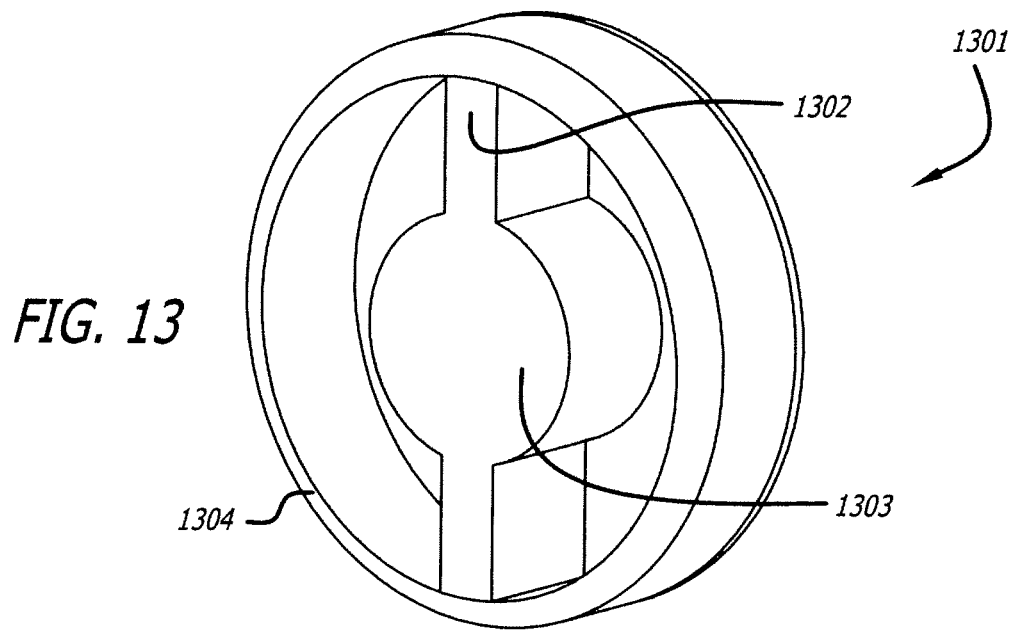
FIG. 13 illustrates an example end cap in accordance with an example embodiment.
Figure 14:
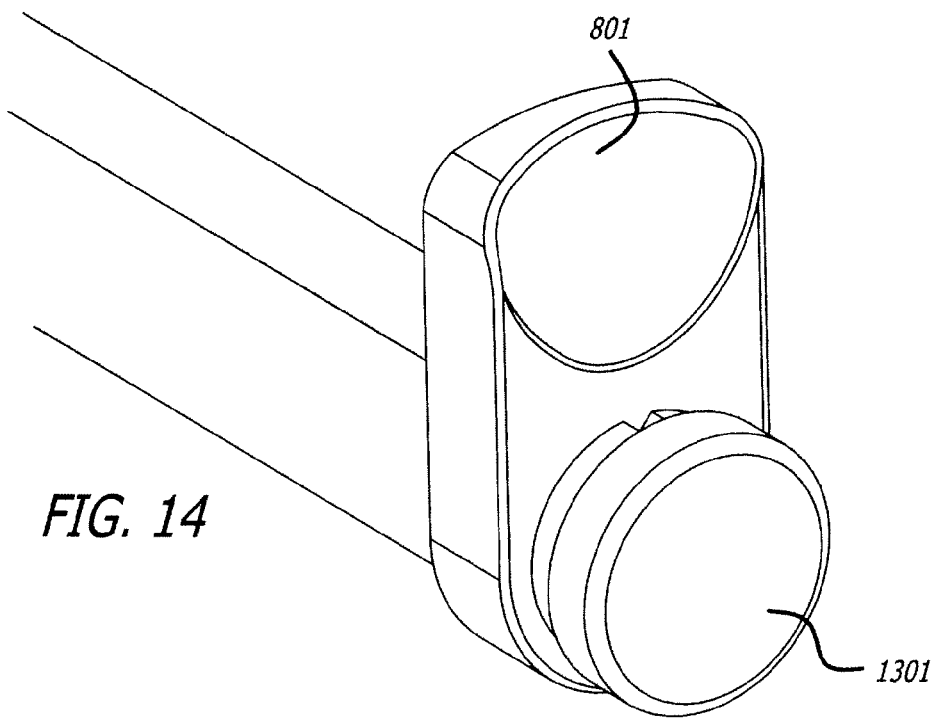
FIG. 14 illustrates an example end cap with an example thumb grip and syringe body in accordance with an example embodiment.

In some example embodiments, an end cap may be included. Such end caps may close the distal end of the syringe body 101 and may prevent the thumb grip 801 from being removed. Such an end cap may be press fit and/or adhered to the distal end of the syringe body 101, or otherwise attached. In addition, it may be comprised of any rigid, semi-rigid, or soft molded materials. An example end cap is shown in FIG. 13. Such a cap 1301 may be generally disk shaped, or may take another shape compatible with the cross-section of the syringe. A distal side of the cap 1301 may be generally flat and solid, while a proximal side of the cap 1301 may include one or more raised features which may fit into and/or around the syringe body 101. For example the end cap 1301 may have a rim 1304 running along an outer perimeter of the cap, which may fit around a syringe body 101, and may also include both a slot plug 1302 and a barrel plug 1303, which may be shaped to fit within the distal end of the syringe body 101. An example cap 1301 is shown in place in FIG. 14, attached to the distal end of a syringe body 101, and preventing the thumb grip 801 from being removed.

Figure 15:
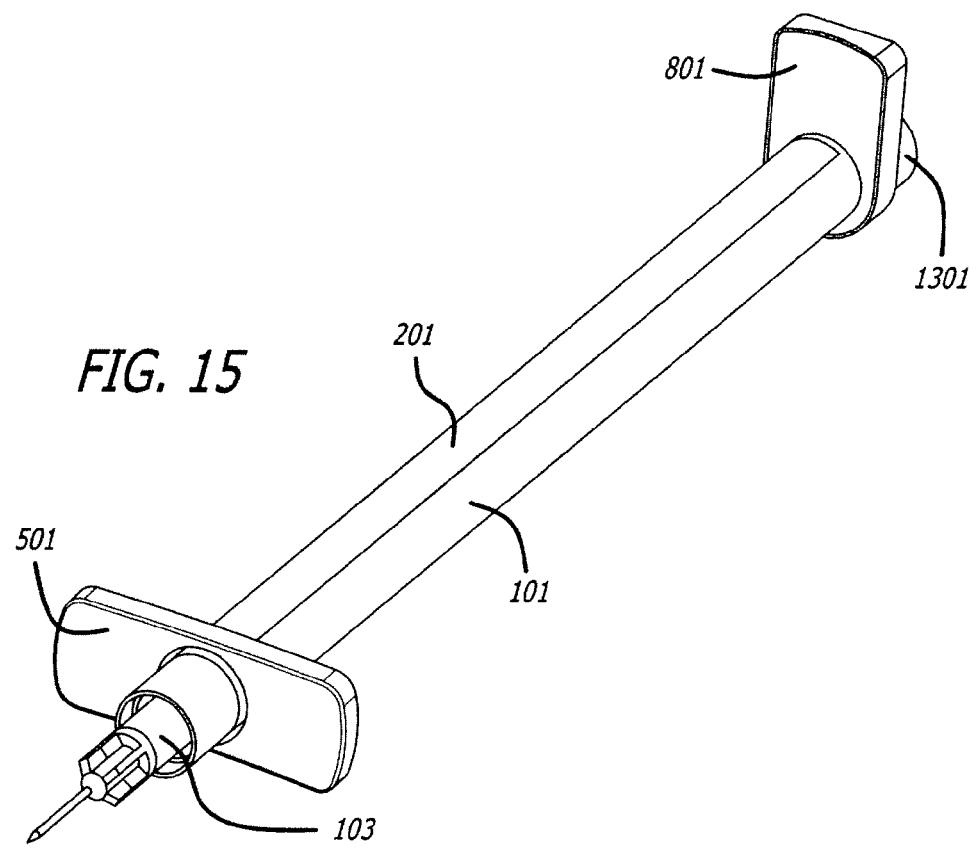
FIG. 15 illustrates an example syringe in accordance with an example embodiment.
Figure 16:
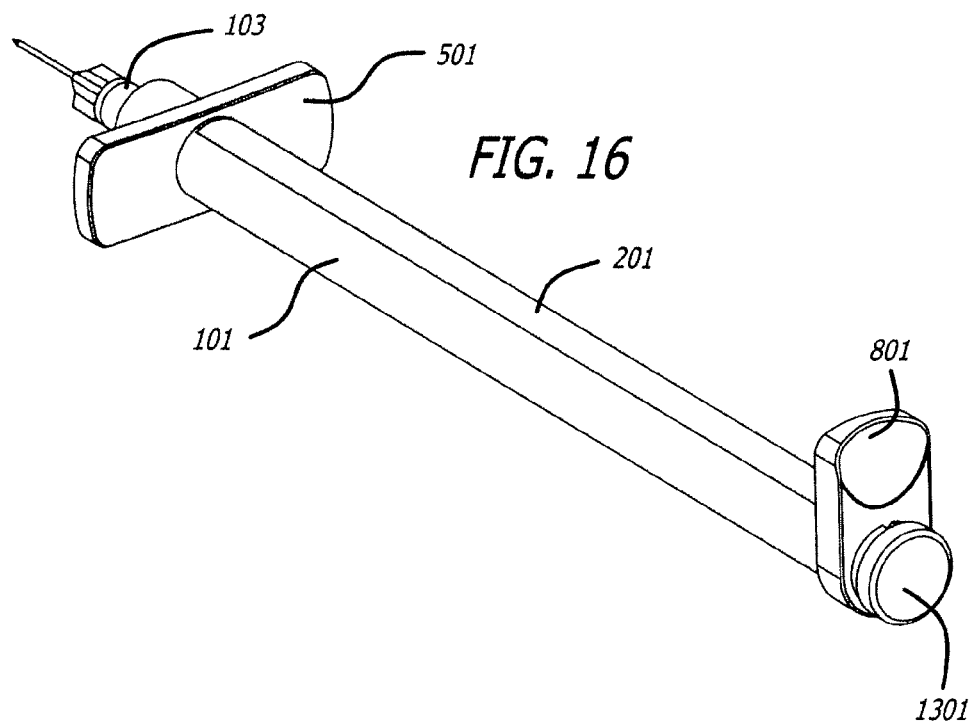
FIG. 16 illustrates an example syringe in accordance with an example embodiment.
Figure 17:
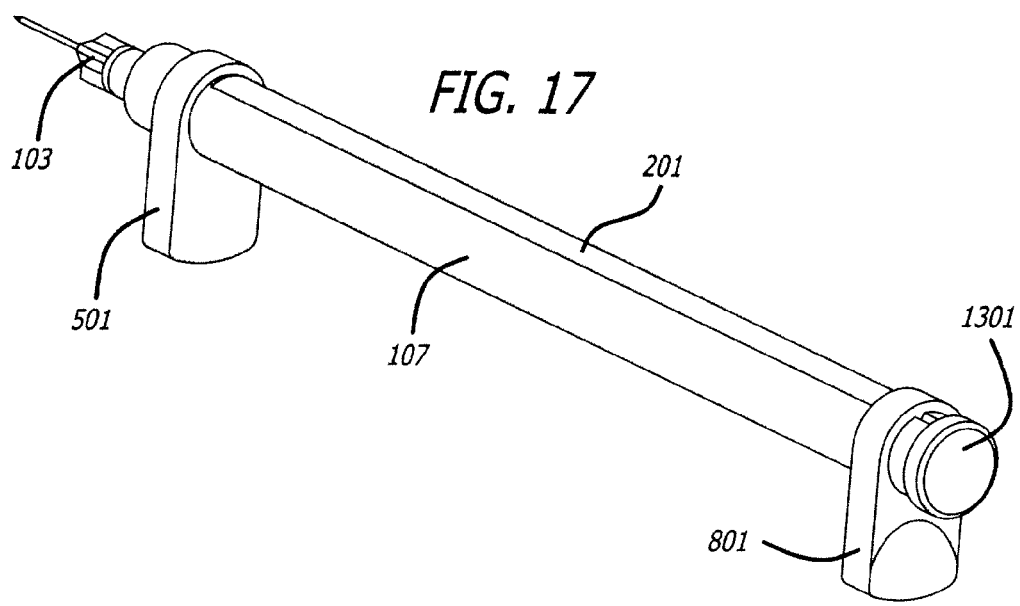
FIG. 17 illustrates an example syringe in accordance with an example embodiment.

An assembled example syringe is illustrated in FIG. 15. The complete assembly includes a syringe body 101, a sleeve 201, a finger grip 501, a thumb grip 801, a plunger 1101, and an end cap 1301. As can be seen, the thumb grip 801 is initially located near the distal end of the syringe body 101. Other views of the example syringe are shown in FIGS. 16-18.

FIG. 19 shows a comparison between an example 0.8 mL syringe 1901, (without sleeve) in accordance with an example embodiment, and a traditional syringe 1902. As can be seen, the traditional syringe 1902 is significantly longer than the example embodiment 1901, as the traditional syringe 1902 requires a lengthy plunger 1903. This additional length may result in reduced user control and comfort.

Figure 20:
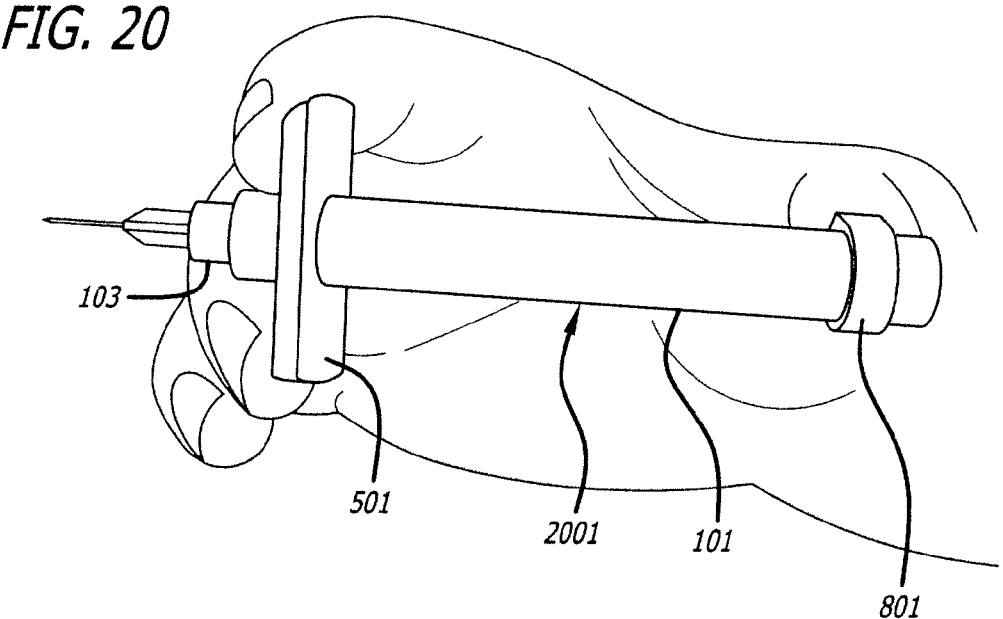
FIG. 20 illustrates an example syringe in accordance with an example embodiment.
Figure 21:
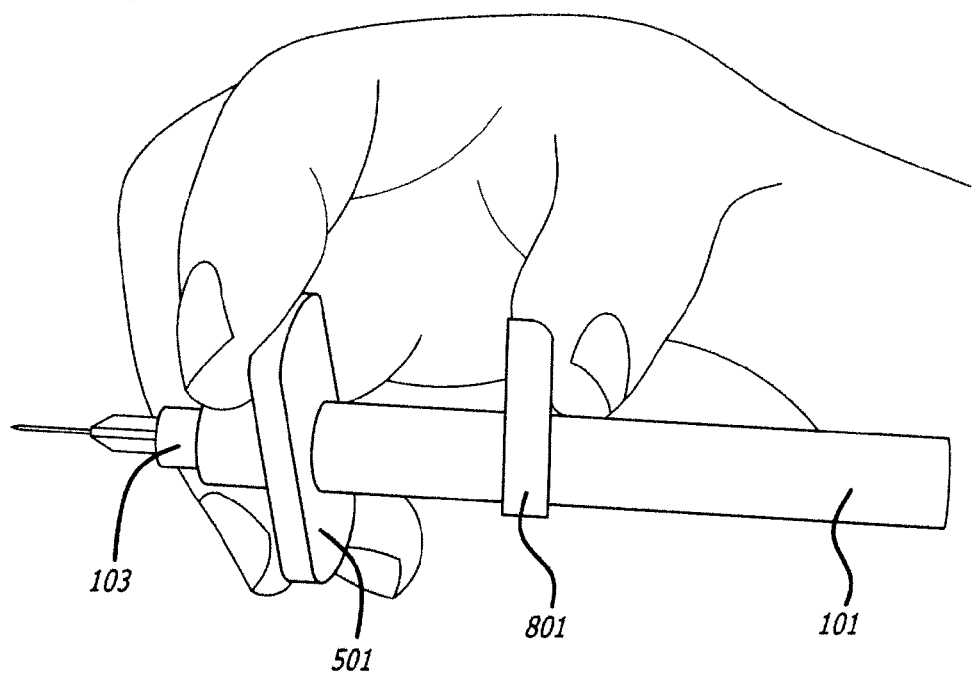
FIG. 21 illustrates an example syringe in accordance with an example embodiment.
Figure 22:
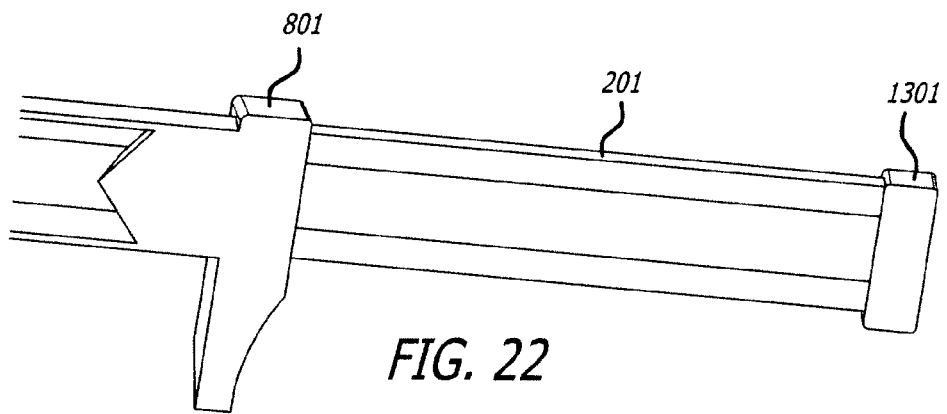
FIG. 22 illustrates a cross-section of an example syringe in accordance with an example embodiment.

FIGS. 20-22 show an example syringe 2001 in use. In FIG. 20 the syringe 2001 is shown in its initial state. The thumb grip 801 has not yet moved. A user may use the syringe 2001 by pressing the thumb grip 801 towards the proximal end of the syringe 2001, using the finger grip 501. For example, the user's forefinger and middle finger may rest on the finger grip component 501, while the user's thumb applies a force to the thumb grip 801.

The applied force on the thumb grip 801 causes the thumb grip 801 to advance forward toward the proximal end of the syringe 2001. During this advance, the cutting edges 901 on the thumb grip 801 cut though the sleeve 201 allow the thumb grip 801 to continue forward without resistance. In addition, the plunger 1101 is moved forward, moving the injectable fluid through the syringe body 101 and out the needle 103.

For example, as shown in FIG. 21, the thumb grip 801 has been moved forward some amount and, therefore, material has been extruded. FIG. 22 shows a similar position in cross-section. As can be seen, the thumb grip 801 has moved forward, and the plunger 1101 has pushed the material in the fluid chamber forward, leaving an empty portion of the fluid chamber, and cutting away a portion of the sleeve 201. It is noted that, as the sleeve 201 is cut by the cutting edge 901, there is a possibility that particulate from the sleeve 201 will fall into the syringe body 101. Such particulate is not a problem, however, because the particulate will be distal to the plunger 1101 and the injectable fluid (i.e. the particulate will not fall into the injectable fluid).

It is noted that, in some cases, a larger fluid injection volume may be needed. This usually requires the syringe to be lengthened and/or the inner diameter to be increased. As explained above, increasing the length of the syringe is typically not practical with a standard medical syringe, because the length of the plunger rod also has to be lengthened. As a result, the distance between the thumb grip on the plunger rod and the finger grip on the syringe would typically be too large for the operator to span their thumb and fingers from one feature (thumb grip on plunger rod) to the other (finger grip on syringe) for a comfortable grip. Increasing the inner diameter is the most common solution, but this will result in a higher extrusion force, which may be impractical, particularly when using high viscosity fluids or gels.

Example embodiments provide for syringes having an intermediate finger grip, which are capable of handling larger volumes of material. The intermediate finger grip can be position adjustable and/or removable, allowing the finger span distance, that is, the distance between the intermediate finger grip and the thumb grip, to be adjusted. This feature allows the operator to inject fluid out of a longer syringe body with an comfortable finger span (that is, the distance between the intermediate finger grip and the thumb grip, without increasing the extrusion force.

Figure 23:
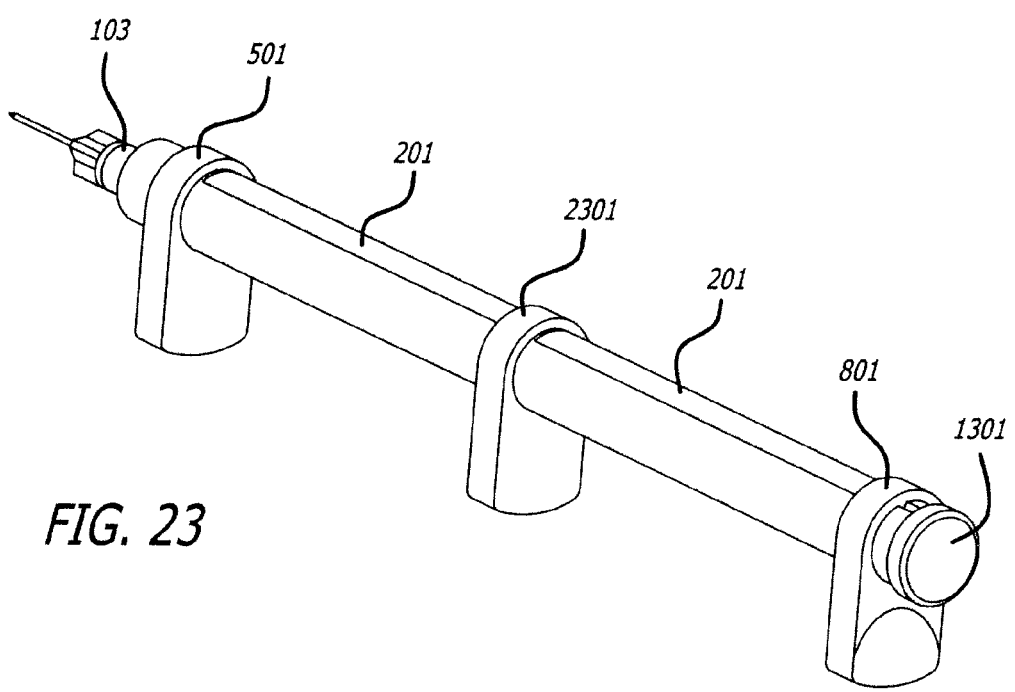
FIG. 23 illustrates an example syringe in accordance with an example embodiment.
Figure 24:
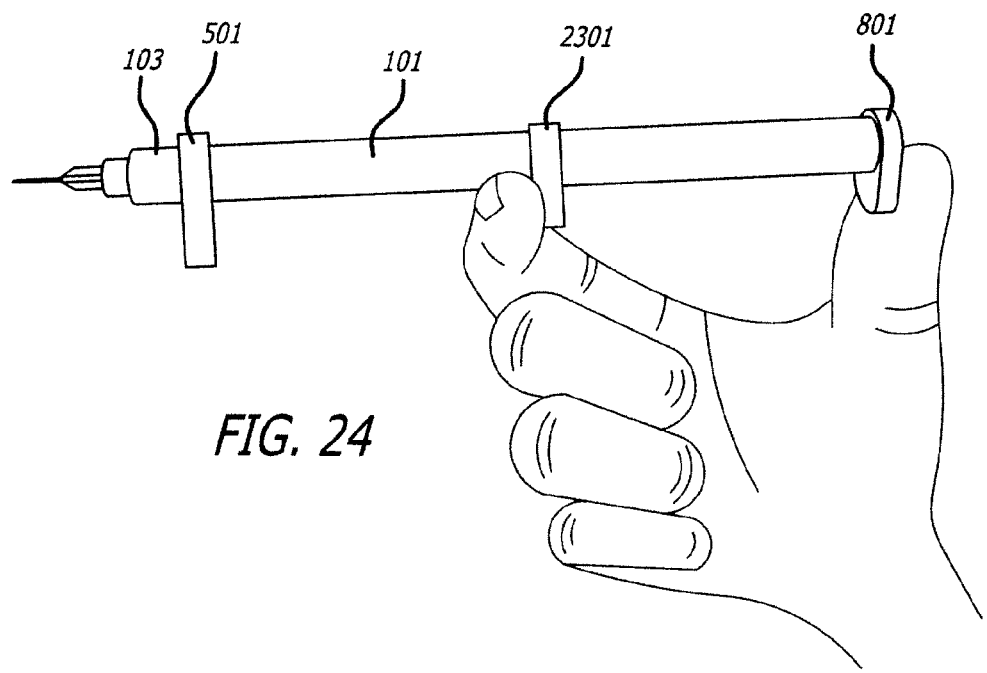
FIG. 24 illustrates an example syringe in accordance with an example embodiment.

For example, FIGS. 23-24 show an example embodiment. The example embodiment may include all of the features described above, and may also include an intermediate finger grip 2301, which may initially be positioned at an intermediate distance along the syringe body. A user may use the syringe as before, except that, in order to maintain a comfortable finger span, the user may first push the thumb grip 801 forward, holding the intermediate finger grip 2301. The intermediate finger grip 801 may be position adjustable and/or removable, allowing the finger span distance to be adjusted.

Figure 25:
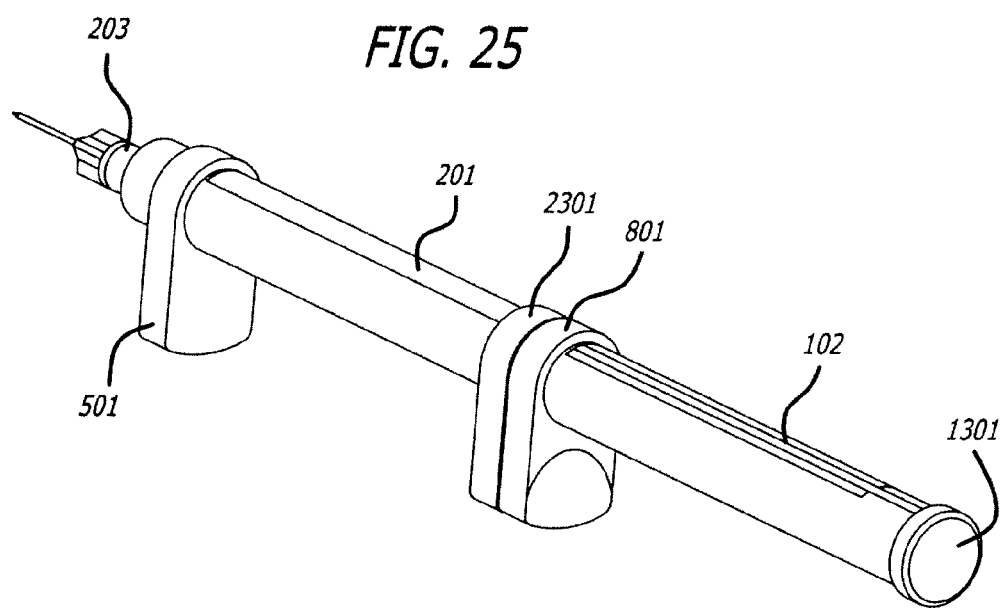
FIG. 25 illustrates an example syringe in accordance with an example embodiment.
Figure 26:
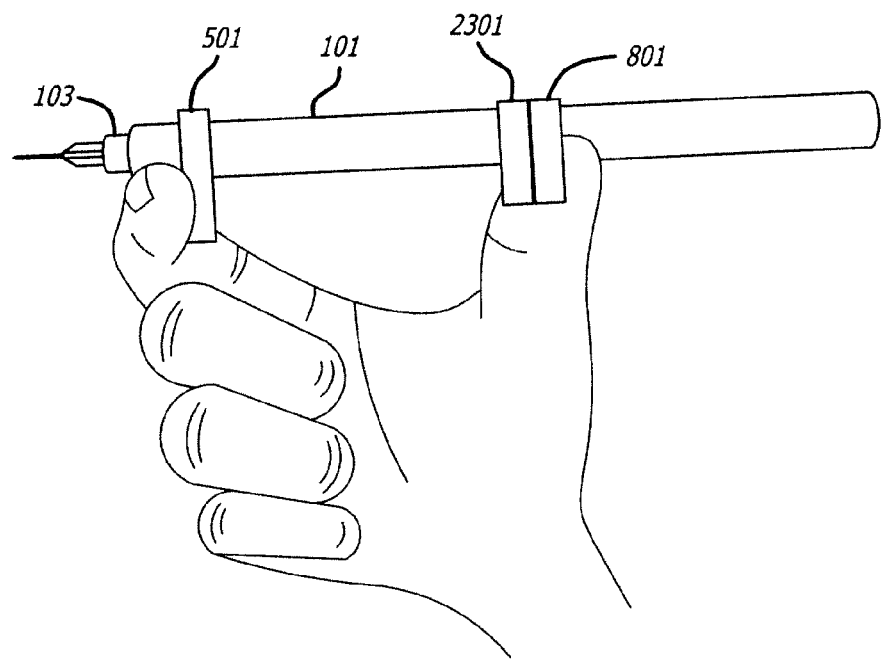
FIG. 26 illustrates an example syringe in accordance with an example embodiment.
Figure 27:
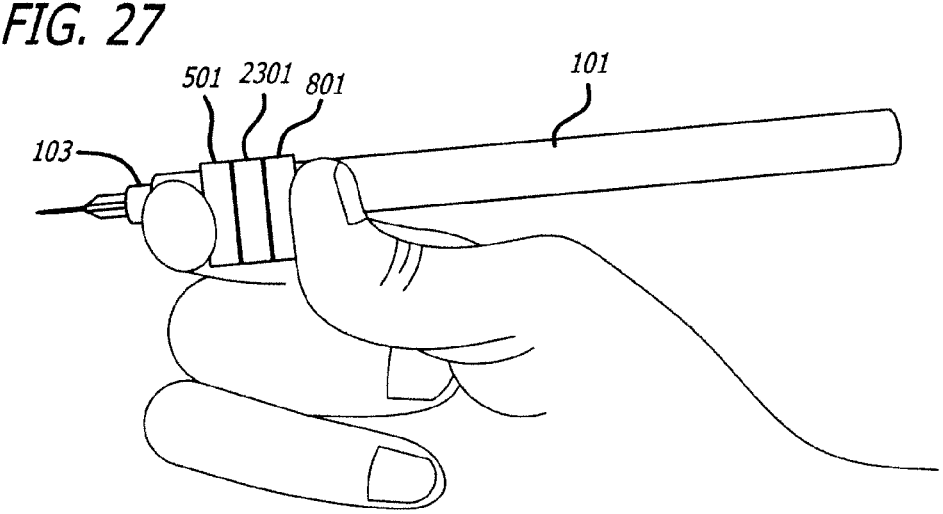
FIG. 27 illustrates an example syringe in accordance with an example embodiment.

The user may continue to push the thumb grip 801 forward until it meets the intermediate finger grip 2301, as in FIGS. 25-26. At that point, the user may change grips, now holding the finger grip 501 and the thumb grip 801. The user may again push the thumb grip 801 forward, which in turn may push the intermediate grip 2301 in front of it, until the two grips reach the finger grip 501, at which point the syringe may be empty, FIG. 27.

Figure 28:
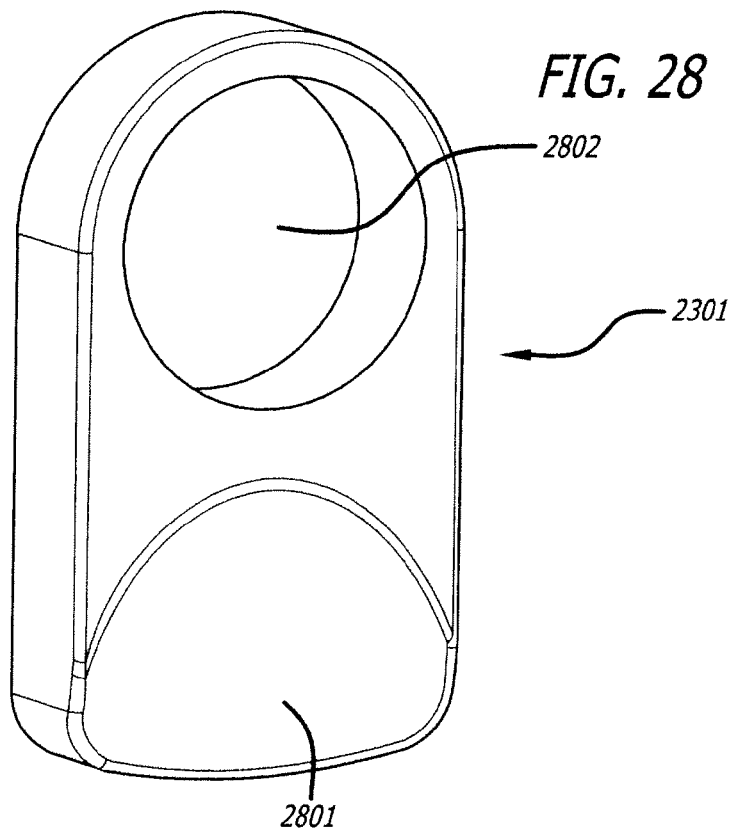
FIG. 28 illustrates an example intermediate finger grip in accordance with an example embodiment.

Like the components discussed above, the intermediate finger grip 2301 may be made from any suitable material. An example intermediate finger grip 2301 is shown in FIG. 28. Such a grip 2301 may have one or more finger cups 2801 to accommodate fingers. In addition, the intermediate finger grip 2301 may have an aperture 2802 shaped to accommodate the syringe body 101. The intermediate finger grip 2301 may be prevented from moving when in use as a finger grip in any reasonable manner. For instance, the intermediate finger grip 2301 may be provided with only one finger cup 2801, and, therefore, when gripped by a user, the user may apply a torque to the intermediate finger grip 2301 which may prevent it from sliding. However, the intermediate finger grip 2301 may slide readily when pushed forward evenly by the thumb grip 801. Alternatively, a locking mechanism may be employed.

Figure 29:
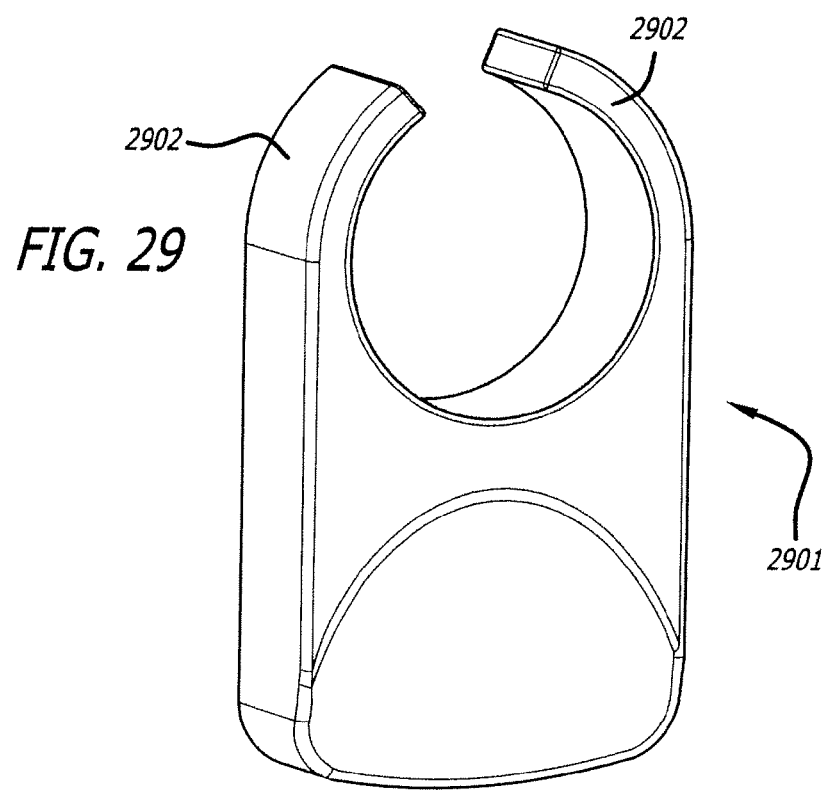
FIG. 29 illustrates an example intermediate finger grip in accordance with an example embodiment.

An alternative, removable intermediate finger grip 2901 is shown in FIG. 29. Such a finger grip 2901 may be similar to the non-removable grip 2301, except that it may be equipped with flexible arms 2902, instead of an aperture 2802, which may clip around the syringe body 101 when in use, but which allow the grip 2901 to be removed once it is no longer needed.

In the preceding specification, the present invention has been described with reference to specific example embodiments thereof. It will, however, be evident that various modifications and changes may be made thereunto without departing from the broader spirit and scope of the present invention. The description and drawings are accordingly to be regarded in an illustrative rather than restrictive sense.

Unless otherwise indicated, all numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A syringe, comprising:
   a syringe body with a fluid chamber, the syringe body having a proximal end and a distal end, with an extrusion opening at the proximal end;
   a first slot formed in the syringe body, starting near the proximal end of the syringe body and ending near the distal end of the syringe body;
   a first sleeve covering the first slot;
   a thumb grip, the thumb grip including a first slot guide disposed in the first slot, the thumb grip shaped to slide from a first position near the distal end of the syringe body toward a second position near the proximal end of the syringe body;
   a plunger disposed in the fluid chamber of the syringe body, the plunger configured to move toward the proximal end of the syringe body in response to pressure applied by a user to the thumb grip, the plunger including a first plunger slot guide disposed in the first slot;
   a finger grip, disposed at the proximal end of the syringe body; and
   an intermediate finger grip, disposed on the syringe body between the thumb grip and the finger grip, the intermediate finger grip comprising
      an intermediate finger grip body shaped to support a user's finger, and
      an aperture passing from a proximal side of the intermediate finger grip body to a distal side of the intermediate finger grip body, in which the syringe body is disposed, wherein the intermediate finger grip is configured to slide toward the proximal end of the syringe body when pushed by the thumb grip.

2. The syringe of claim 1, wherein the intermediate finger grip is configured to be removed from the syringe body during operation.

\* \* \* \* \*